United States Patent [19]

Szabo

[11] 4,283,199
[45] Aug. 11, 1981

[54] METHOD OF RESOLVING BIOLOGICAL SOLUTIONS

[75] Inventor: Elek I. Szabo, Brighton, Mass.

[73] Assignee: Forsyth Dental Infirmary for Children, Boston, Mass.

[21] Appl. No.: 67,947

[22] Filed: Aug. 20, 1979

[51] Int. Cl.³ .................... B01D 15/00; B01D 15/08; G01N 31/06; G01N 33/48

[52] U.S. Cl. ................ 23/230 B; 210/656; 422/70; 422/101; 422/256

[58] Field of Search ............... 23/230 B; 422/70, 50, 422/255, 256, 101; 210/31 C

[56] References Cited

U.S. PATENT DOCUMENTS

| | | | |
|---|---|---|---|
| 3,765,461 | 10/1973 | Keck | 422/70 X |
| 3,966,410 | 6/1976 | Jahnsen | 23/230 B |
| 4,055,510 | 10/1977 | Peska et al. | 210/31 C X |
| 4,066,879 | 1/1978 | Leaver et al. | 422/70 X |
| 4,143,201 | 3/1979 | Miyashiro et al. | 210/31 C |

OTHER PUBLICATIONS

Lakshmanan et al., "An Improved Method of Gradient Elution Chromatography & Its Application to the Separation of Urinary Ketosteriods", Archives of Biochemistry & Biophysics, vol. 53, No. 1, Nov. 1954, pp. 258–281.

Primary Examiner—Arnold Turk
Attorney, Agent, or Firm—Richard P. Crowley

[57] ABSTRACT

A method of resolving biological solutions which comprises forming extracting and separating zones in a cellulose-packed chromatographic column and separating the components of the adsorbed sample solution from the top extraction zone by the use of solvents of increasing or decreasing polarity and recovering separate effluent fractions from the column.

14 Claims, 1 Drawing Figure

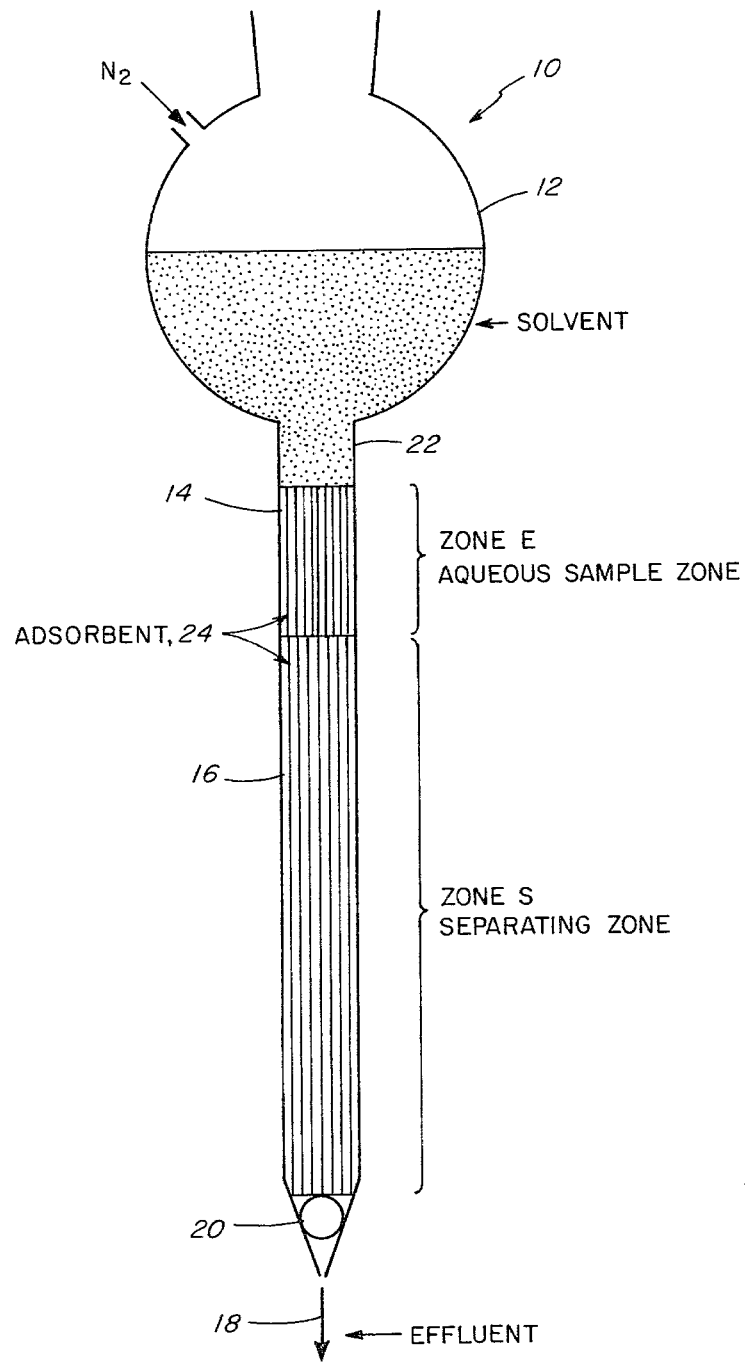

METHOD OF RESOLVING BIOLOGICAL SOLUTIONS

BACKGROUND OF THE INVENTION

An often recurring problem for the researcher, whether he be working in the university or industry, is the need to remove one or only a few specific substances from a solution admixed with a large variety of other solutes of no interest. In some cases, the desired component(s) may be known beforehand, and the objective is one of isolation and purification of desired quantities. A problem of this type is presented by the isolation of opioid alkaloids from the milky exudate of the poppy plant. In other cases, one may be faced with unknowns as regards the number, as well as the identity, of the solutes of interest, and the objective is to ascertain both. Identification of the urinary metabolites of an experimental drug would illustrate the problem in the second type of cases.

There are certain inherent difficulties in the problem under consideration which have defied the development of a simple and satisfactory method applicable in most such cases. The commonalities underlying the problem at hand are: (1) presence of water; (2) presence of inorganic salts; and (3) the multitude and diversity of compounds present with dissimilar and similar properties (chemical and physical) to the solute(s) of interest. In addition, not infrequently the task of selective isolation is further exacerbated by extremely low concentrations of those solutes relative to totally dissolved material.

In contrast, most methods of separation depend upon the availability of narrowly defined classes of purified components as starting materials. As examples constituting such classes may be mentioned amino acids, carbohydrates, lipids, etc. The presence of other substances, with differing physical and/or chemical properties, may preclude the employment of separation techniques otherwise appropriate to the task. For example, water present in an incompletely dried lipid sample would deactivate silicic acid (choice of adsorbent for chromatography of lipids), resulting in loss of adsorption and separation of components. Should the components of interest be present in very low concentrations, a prepurification (enrichment) step may be required, if for no other reason than to prevent overloading the system of separation employed, while trying to achieve detectable levels. For example, drug levels in body fluid are often too low to permit their direct use for GLC, even if the various other components present did not interfere with the conditions of analysis.

For the reasons mentioned above, it is, therefore, not surprising that no general one-step procedure has been developed, applicable to and capable of resolving complex aqueous solutions as characterized in the foregoing. Usually a multistep procedure is employed. The particular approach chosen is usually determined by the nature of the solutes of interest.

A common starting step is multiple solvent extraction of the sample. Often the pH is adjusted for preferential partitioning which further may be enhanced by additions of strong electrolytes. When dealing with unknowns, extractions are carried out at three pH ranges; that is, acid, neutral and alkaline. When extractions by solvents as described do not prove satisfactory, the sample is subjected to chemical or enzymatic hydrolysis, followed by reextraction. Continued failure of extraction at this point would necessitate recourse to other methods.

Some of the salient drawbacks associated with solvent extraction are the following. To obtain a relatively clean and near complete extract of the desired solute(s) is more of an event in serendipity than a virtue of the method. Usually the extract contains some of the desired solute(s), but the bulk is extraneous matter. Moreover, solutes of interest present in the extract reflect not so much their proportional concentrations in the sample, but rather their partition coefficients under the conditions of extraction. Unless the latter is known to start with, no conclusion can be drawn as to the quantitative distribution of the solutes of interest in the sample. If the desired components are of semipolar or polar character, extraction is usually incomplete, resulting not only in waste of material, but also in the need for larger sample size.

The process of extraction often is difficult to perform. Especially solutions of biological origin, when shaken with nonmiscible solvents, tend to form emulsions. This may be so severe as to prevent the applicability of the method or may require additional drastic measures. Finally, the extracts so obtained often require extensive further purification.

Ion-exchange resins also are employed for the selective isolation of solutes. By suitable manipulation of pH and buffer strength, one may obtain enriched fractions of the desired components. Here again there are certain difficulties. Use of buffers may increase the electrolyte content in the eluates, requiring additional procedures for their removal. Strong ion-exchange resins may act as strong acids or bases, resulting in hydrolysis or chemical breakdown of sensitive materials. They are stable only to varying degrees, and subunits of their matrix can contaminate the effluents. The resins, apart from the functional groups they possess, may act as nonspecific adsorbents and thus introduce an additional variable.

In view of the lack of methodology capable of resolving complex biological fluids into their components or at least into narrow classes with only a few constituents, efforts were directed at total analysis in one step. Earlier, Dalgliesh (*Biochem. J.*, 1966, 101, 792) extracted whole urine under drastic conditions, treated the residue with a variety of derivatizing reagents and analyzed the resultant derivatives by GLC. More recently, Thompson (*Res. Comm. Chem. Path. and Pharm.*, 1977, 16, 145) went a step further by attempting GLC analysis of total urinary residue without any preliminary purification or separation.

Some of the obvious drawbacks of such an approach immediately should be apparent: (a) unknown metabolites may escape detection, since there is no universal derivatizing reagents; (b) such analyses are time-consuming, due to the large number of compounds that do get derivatized; (c) column life is greatly shortened by injection of salts and other underivatizeable compounds; and (d) perhaps most importantly the chromatograms so obtained often cannot be interpreted meaningfully. A glance at such a chromatogram would reveal that the density of information provided is so great as to preclude both quantitative and qualitative assessment of individual components. Frequent partial or complete overlaps obscure detection of components, and the range of concentrations usually encountered exceed the linearity of the detection systems employed. This complicated picture further may be confused by the likely presence of spurious peaks, due to the well-known tendency of some of the commonly used derivatizing reagents to produce multiple derivatives from single compounds.

SUMMARY OF THE INVENTION

A new method for the resolution of complex solutions, particularly solutions and the effluent or fractions recovered in the method, of biological origin involves particularly the resolution and identification of biological solutions. The method presented is based on the properties of such a complex solution containing, in addition to water or other solvent, a diversity of organic compounds and inorganic salts.

In my method, no single one term can characterize adequately the method and the mode of operation of the column. The nature of the problem demanded an approach incorporating the simultaneous operation of several principles of separating techniques. The solution to the problem first had to be conceived conceptually, while the actual development of the method involved the physical design in conformity with the principles imposed.

The underlying operational principles include:
I. Extraction
  (a) partitioning
  (b) salting out
II. Chromatographic separation
  (a) partitioning
  (b) adsorption-desorption
III. Role of support
IV. Polarity gradient.

At the time of initial conditions; that is, after having applied the aqueous solution to be separated and the first eluant, the column may be divided from an operational point of view into two segments as shown in the drawing. These are the extracting and separating zones (for short zones E and S). At zero time, zone E and the overlayered solvent could be regarded as one plate for the partitioning of the solutes present in the aqueous zone. With somewhat of an oversimplification, it could be compared to the distribution of the solutes in biphasic systems in a separating funnel. However, time is not allowed for an equilibrium to be established under those stationary conditions, because the eluant begins its downward passage as soon as applied. This movement has the effect of establishing more plates for partitioning, as fresher layers of solvents keep replacing those moving ahead. The net result is efficient extraction of the aqueous zone by the particular solvent passing through for which some of the solutes happen to possess favorable partition coefficients. It follows, therefore, that the number of solutes so extracted may be increased or reduced, depending on whether the incremental change in polarity of the passing solvent was made large or small.

After passage of a particular eluant, the process of its separation begins in zone S. What begins at the aqueous boundary is the chromatographic separation of a narrow class of solutes. Further, this process of separation cannot now be interfered with by the multitude of other components present originally in the sample, as they have been left behind in the aqueous zone, awaiting their turn of extraction by an appropriate solvent system to follow.

As the eluants are gradually becoming more polar, they will have an increasing capacity to dissolve water. At the same time and for the same reason, water present in zone E will dissolve increasing amounts of the more polar solvents. The net effect of these changes taking place in opposite directions is an enhanced partitioning of solutes from the aqueous phase into the moving solvent phase. This process is further accelerated by the salting-out effect, due to increasing concentrations of the inorganic salts as the volume of the aqueous phase keeps getting smaller. The result of the confluence of these several processes is the serial extraction of all the components of the sample ranking according to their polarity and inclusive of those with the highest degree uncontaminated by one another.

The separating zone is presumed to function initially primarily by the principles of adsorption chromatography, as there is insufficient water available for a stationary phase to form (the crystalline water present in cellulose is in a different domain). However, as more water is eluted and subsequently largely readsorbed on the surface of the cellulose particles, increasingly conditions are created for separation by partition chromatography. Here again the strongly polar (and thus hydrophilic) solutes are moved along for the same reasons as they get extracted, and similar considerations apply as described above. In short, conditions are created for the chromatographic resolution of solutes in the separation zone by the existence of a biphasic system of changing character throughout its length. Further, as a consequence of the initial conditions chosen, a polarity difference is established and maintained between the phases, permitting separation of the extracted solutes.

In the present case, indirect evidence suggests that even the inorganic salts eluted lastly undergo varying degrees of fractionation.

The advantages of my method of resolution comprise: very little expense is involved in using the method. Cellulose powder (microcrystalline) and such common solvents as benzene, ethyl acetate and methanol are the main requirements, in addition to the commonly available chromatographic columns. The latter can be homemade with a minimum of skill; the results are highly reproducible under specified conditions; quantitative recovery is an inherent aspect of the method and was always observed; as a consequence of the above, no sample material is wasted. Also, for the same reason, smaller sample sizes may be used as compared to other methods; no drastic conditions are necessary for the isolation of the more polar solutes, and thus the risks of chemical changes brought about by the methods employed are avoided; the fractions as obtained are ready for further analysis; and the method is easily adaptable as regards sample size and degree of resolution. Thus my method permits the simple, effective and rapid resolution of biological solutions.

BRIEF DESCRIPTION OF THE DRAWING

The drawing is a schematic illustrative drawing of the apparatus employed in the method of the invention.

DESCRIPTION OF THE EMBODIMENTS

The drawing shows apparatus 10 with a solvent-container bulb 12 at the top for the introduction of each selected solvent to the top of the column 22. The column is packed with cellulose powder 24 as an adsorbent, with the column 22 being divided into zones 14 (zone E) and 16 (zone S). The end of the column contains a porous material, such as a glass wool plug 20, and effluent 18 is discharged from the column. Zone E contains the adsorbent with the aqueous sample material, while zone S contains the adsorbent and the particular solvent eluant from zone E.

My invention will be described in connection with its preferred embodiment and for the resolution of a specific solution; however, it is recognized that other solutions, biological and non-biological, aqueous and nonaqueous, may be resolved employing my method. For example, my method is particularly applicable to the resolution of solutions, such as spinal fluid, blood serum, lymph fluid, animal or plant tissue extracts, such as aqueous or saline extracts, complex saline pharmaceutical solutions and the like.

A wide variety of solvents may be employed in my method, alone or in combination, to obtain solutions of varying polarity and to obtain various effluent eluted fractions, depending on the solution to be resolved. For example, nonpolar solvents, alone or saturated with water, such as aromatic solvents, toluene, xylene, benzene, or aliphatic solvents, such as hexane, cyclohexane, pentane, octane, etc., may be used, while increasing polarity may be obtained with esters, ethers, like ethyl ether, ketones, like acetone, alcohols, such as ethyl acetate, lower alkanols, such as methyl, ethyl and propyl alcohol, glycols, acetic acid, and chloro and fluorohydrocarbons.

Desirable solvents to be used include those solvents which are nontoxic, nonreactive, volatile, possess low viscosity and from which the residue can be recovered easily. If desired, the solution to be resolved may be nonaqueous and water and aqueous solutions may be employed as the solvent. The preferred adsorbent material is cellulosic in nature, such as cellulose or cellulose derivatives, but my method is not restricted only to cellulosic materials.

My method is based on direct column chromatography of biological fluids employing microcrystalline cellulose as the adsorbent. A slurry is prepared by adding the cellulose powder to benzene and the trapped air is removed by 5' sonication to prevent bubble formation on the column. A regular chromatographic column made of glass is then packed to a height of 12 cm under slight $N_2$ gas pressure. For purposes of standarization and as a point of reference, an internal diameter of 8 mm (OD 10 mm) was chosen. For the same reasons, 1 ml of an aqueous solution to be resolved was applied to such a column which appeared optimal. This volume of solution penetrated into the adsorbent to a depth of 3 cm. Separation of solutes is accomplished by elution with successive volumes of solvents of increasing polarity encompassing the polarity scale from benzene to water (in the present case). For example, the solvent for an aqueous solution may comprise in sequence a hydrocarbon, such as benzene saturated with water, then an ester, such as ethyl acetate saturated with water, and then the ethyl acetate with increasing volumes of methyl alcohol, then acetic acid and water. In the present case for the column as specified above, 10 ml volumes were applied for each incremental step in polarity, and 14 fractions were taken. Fractionation of whole rat urine on microcrystalline cellulose column and elution or urinary metabolites of an experimental drug labeled with $C^{14}$ are shown in Tables I and II.

TABLE I

Eluting Solvent Systems in Order of Use:
Solvent volume: 10 ml per fraction
Column 12 × 1* cm., packed in benzene. 1 ml volume of urine applied.

| | | | | |
|---|---|---|---|---|
| (1) | 57 μl | HAc + | $Bz(H_2O)$ | 10 ml |
| (2) | 85.5 | HAc + | $EA(H_2O)$ | 10 ml |
| (3) | 114 | HAc + | 0.25ml MeOH + $EA(H_2O)$ to 10 ml | |
| (4) | 143 | HAc + | 0.5ml MeOH + $EA(H_2O)$ to 10 ml | |
| (5) | 172 | HAc + | 1.0ml MeOH + $EA(H_2O)$ to 10 ml | |
| (6) | 200 | HAc + | 2.0ml MeOH + $EA(H_2O)$ to 10 ml | |
| (7) | 229 | HAc + | 4.0ml MeOH + $EA(H_2O)$ to 10 ml | |
| (8) | 257 | HAc + | 6.0ml MeOH + $EA(H_2O)$ to 10 ml | |
| (9) | 286 | HAc + | 8.0ml MeOH + $EA(H_2O)$ to 10 ml | |
| (10) | 315 + 0.5ml $H_2O$ + 1.5ml $EA(H_2O)$ + MeOH to 10 ml | | | |
| (11) | 9ml MeOH + 1ml $H_2O$ (wash) | | | |
| (12) | 8.5ml MeOH + 1ml $H_2O$ + 0.5ml DEA | | | |
| (13) | 8.5ml MeOH + 1ml $H_2O$ + 0.5ml DEA | | | |
| (14) | 8.5ml MeOH + 1ml $H_2O$ + 0.5ml DEA | | | |

*OD

Abbreviations for Table I:
HAc: glacial acetic acid
Bz: benzene
$Bz(H_2O)$: Benzene saturated with water
EA: Ethyl acetate
$EA(H_2O)$: Ethyl acetate saturated with water
DEA: diethylamine
μl: $10^{-6}$ liter
MeOH: Methanol

TABLE II

| Total cpm in Fractions | Percent of $C^{14}$ labeled in Fractions |
|---|---|
| (1) 195 | .5 |
| (2) 8780 | 21.2 |
| (3) 1515 | 3.7 |
| (4) 360 | 0.9 |
| (5) 1420 | 3.4 |
| (6) 1510 | 3.6 |
| (7) 785 | 1.9 |
| (8) 2280 | 5.5 |
| (9) 2950 | 7.1 |
| (10) 1350 | 3.3 |
| (11) 1500 | 3.6 |
| (12) 18360 | 44.2 |
| (13) 270 | 0.6 |
| (14) 230 | 0.5 |
| 41505 | 100.00% |

Total cmp in 1 ml urine: 43800
Recovered cpm: 41505 or 95%. Counts of individual fractions were not corrected for efficiency. However, correction shows 100% recovery.
cpm: counts per minute When finer resolution was desired, either smaller volumes of the effluent were taken or the polarity gradient was adjusted to rise less sharply or both effects were combined.

The foregoing procedure yielded fractions from complex biological solutions of high enough purity, with only a few constituents present to permit direct application of the usual techniques of identification, such as thin-layer chromatography (TLC), gas-liquid chromatography (GLC), GLC-Mass spectroscopy, nuclear magnetic resonance (NMR), infrared or ultraviolet (IR-/UV), etc.

Various modifications may be made in the basic method, such as the use of multiple chromatography columns, or steps, variation in pH, variation in column size, variation in sample concentrations, alone or in combination.

In my method, if further reduction of extraneous components is desired which coelute with the solute of interest, the corresponding fraction may be rechromatographed. This is done by evaporation of the solvent, redissolving the residue in water, applying the solution onto a columm of appropriate size (usually smaller than in the first run), followed by elution of the column. However, preceding by one or two steps relative to its prior emergence, eluants of gradients with shallower slope should be used.

Solubility and thus the partition coefficients of solutes often can be altered greatly by changes in pH, and advantage is taken of this fact in the present method. Elutions can be carried out with acid, alkaline or neutral solvents. Changes in pH may be introduced during the course of a run. However, in the latter case, a neutral solvent step should be introduced in the elution sequence to avoid salt formation due to overlap in pH. For obvious reasons, it is best to employ volatile acids or bases, as they leave no residue after evaporation. Some of these include, but are not limited to: acetic acid, diethylamine and ammonium hydroxide.

The column diameter and length may vary. The largest column used had an ID of 22 mm accomodating 4.8 ml sample size, while the smallest one was of 6 mm ID with 0.36 ml volume of sample. In both cases, the height was maintained at 12 cm. The volumes of the eluants were adjusted accordingly, which varied as the square of ratios of the radii relative to the standard (ID=8 mm).

My column has been described employing a microcrystalline cellulose as the preferred adsorbent; however, other polysaccharide support adsorbents may be employed alone or in combination with other adsorbents, such as starch (amylo pectin) or starch derivatives and various dextrans and dextran derivatives.

The biological fluid most used in the development of the present method was rat urine applied directly as is. Its solid content was determined by lyophylization of 100 ml volume to dryness and was found to be 8.3 g or 83 mg/ml. A tenfold concentrate was prepared by addition of distilled water having a calculated content of solids of 830 mg/ml. Onto the standard column, 1 ml of the concentrate was applied and eluted as before. While the urinary components showed similar pattern of emergence, as in the case of normal urine, there was, however, a shift and some spreading out observable. It appears that, in the present case at least, fivefold to sevenfold concentration of the sample would not exceed optimal solute load. Using the available data for rat urine, this would represent a solute load of 415 to 581 mg per ml.

What I claim is:

1. A one-step method for the extraction and separation of an aqueous complex solution of biological origin into all of its constituent fractions in a single column, which method comprises:
   (a) introducing a predetermined volume of an aqueous solution of biological origin, having a plurality of organic compounds and inorganic salts therein, into the top of the column, which column contains a water-adsorbent support material, to provide an upper extraction zone and a lower separation zone in the column, with the water of the solution adsorbed onto the support material to form the extraction zone;
   (b) introducing into the top of the column successive predetermined volumes of solvents as eluants, the solvents of selected and sequentially increasing polarity to pass the solvents through the extraction zone to form, below the lower aqueous boundary layer of the extraction zone, a chromatographic separation zone in the column;
   (c) adsorbing the water of the aqueous solution onto the support material in the extraction zone and sequentially extracting in the extraction zone, by the successive volumes of solvents through liquid partitioning, discrete, moving, solute fractions of increasing polarity;
   (d) directly introducing the successive solute fractions into the lower separation zone from the upper extraction zone, to provide for the chromatographic resolution of the solute fractions into solute-eluant fractions of increasing polarity in the separation zone, the resolution of the solute fractions initially occurring by chromatographic adsorption and later with solute fractions of increasing polarity, resolution of the solute fractions by liquid-partition chromatography; and
   (e) removing the resolved eluant fractions of defined increasing polarity from the lower portion of the separation zone, thereby providing for the simple, effective and quantitative extraction and resolution of the solution into eluant fractions.

2. The method of claim 1 which includes employing a powdered cellulosic material as the adsorbent support material.

3. The method of claim 1 which includes employing a microcrystalline cellulosic material as the adsorbent support material.

4. The method of claim 1 wherein the solution comprises a urine, spinal fluid, blood serum, tissue extracts or lymph fluid.

5. The method of claim 1 which includes introducing solvents as eluants of increasing polarity from about the polarity of benzene to about the polarity of water.

6. The method of claim 1 wherein the solvents comprise benzene, ethyl acetate, methanol, acetic acid and water.

7. The method of claim 1 which includes employing a powdered starch material as the adsorbent support material.

8. The method of claim 1 which includes identifying at least one of the eluant fractions removed from the column.

9. The method of claim 1 which includes introducing solvents of different pH values and employing a neutral solvent between uses of solvents of different pH.

10. The method of claim 9 wherein the solvents are volatile acids or bases which leave no residue or evaporation.

11. The method of claim 1 which includes:
    (a) removing the solvent of a selected eluant fraction to obtain the residue thereof;
    (b) redissolving the residue in water to form a new solution; and
    (c) introducing the new solution into the top of the column as the solution and repeating the extraction and resolution of the new solution, to obtain a new eluant fraction with reduced extraneous components.

12. The method of claim 11 which includes employing a column for the new solution which has a smaller diameter than the diameter of the column employed, to obtain the original eluant fraction.

13. The method of claim 11 which includes employing a volatile solvent and removing the solvent by evaporation to form the residue.

14. A one-step method for the extraction and separation of an aqueous complex solution of biological origin into all of its constituent fractions in a single column, which method comprises:

(a) introducing a predetermined volume of an aqueous solution of biological origin into the top of the column, which solution is selected from the group consisting of urine, spinal fluid, blood serum, tissue extracts and lymph fluid, and which column contains a water-adsorbent, microcrystalline cellulosic support material, to provide an upper extraction zone and a lower separation zone in the column, with the water of the solution adsorbed onto the support material to form the extraction zone;

(b) introducing into the top of the column successive predetermined volumes of solvents as eluants, the solvents of selected and sequentially increasing polarity of from about the polarity of benzene to about the polarity of water, to pass the solvents through the extraction zone to form, below the lower aqueous boundary layer of the extraction zone, a chromatographic separation zone in the column;

(c) adsorbing the water of the aqueous solution onto the support material in the extraction zone and sequentially extracting in the extraction zone, by the successive volumes of solvents through liquid partitioning, discrete, moving, solute fractions of increasing polarity;

(d) directly introducing the successive solute fractions into the lower separation zone from the upper extraction zone, to provide for the chromatographic resolution of the solute fractions into solute-eluant fractions of increasing polarity in the separation zone, the resolution of the solute fractions initially occurring by chromatographic adsorption and later with solute fractions of increasing polarity, resolution of the solute fractions by liquid-partition chromatography; and (e) removing the resolved eluant fractions of defined increasing polarity from the lower portion of the separation zone, thereby providing for the simple, effective and quantitative extraction and resolution of the solution into eluant fractions.

* * * * *